United States Patent [19]

Kubota et al.

[11] Patent Number: 5,041,440

[45] Date of Patent: Aug. 20, 1991

[54] DITHIOLANE DERIVATIVES

[75] Inventors: Shuhei Kubota; Kunikazu Hiraga, both of Osaka; Keisuke Nakayama; Matazaemon Uchida, both of Kawachinagano, all of Japan

[73] Assignee: Nihon Nohyaku Co., Ltd., Tokyo, Japan

[21] Appl. No.: 396,665

[22] Filed: Aug. 22, 1989

[51] Int. Cl.$^5$ .................. C07D 413/04; C07D 413/14; C07D 339/06; A61K 31/385
[52] U.S. Cl. .............................. 514/231.5; 514/232.2; 514/442; 544/111; 544/145; 544/374; 549/38; 546/207; 546/208
[58] Field of Search ...................... 514/442, 231.2, 326, 514/255, 252; 549/38; 544/145, 374

[56] References Cited

U.S. PATENT DOCUMENTS

| | | | |
|---|---|---|---|
| 4,535,075 | 8/1985 | Kurono et al. | 514/99 |
| 4,668,799 | 5/1987 | Yoshizawa et al. | 514/252 |

FOREIGN PATENT DOCUMENTS

| | | |
|---|---|---|
| 3323105 | 1/1984 | Fed. Rep. of Germany . |
| 63-60983 | 3/1988 | Japan . |

OTHER PUBLICATIONS

Morrison and Boyd, *Organic Chemistry*, 4th Ed. (1983), Allan and Bacon, Inc., p. 894.
Chemical Abstract, Dec. 1988, vol. 109, No. 23, p. 667, Abstract No. 211056E.

*Primary Examiner*—Mukund J. Shah
*Assistant Examiner*—Philip Datlow
*Attorney, Agent, or Firm*—Cushman, Darby & Cushman

[57] ABSTRACT

Novel dithiolane derivatives of formula:

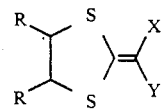

wherein X is, a $C_2$–$C_7$ alkylcarbonyl group, benzoyl group, benzoyl group substituted with 1-3 groups selected from halogen, $C_1$–$C_4$ alkyl, and $C_1$–$C_4$ alkoxy; Y represents $C_2$–$C_7$ alkylcarbonyl group, $C_2$–$C_7$ alkoxycarbonyl group or cyano group; and R represents di ($C_1$–$C_4$ alkylamino) group, morpholino group or piperidino group, are produced by reacting glyoxal sodium bisulfite adduct with amine compounds in the presence of acids and then with dithiolates. The dithiolane derivatives can activate liver functions and are effective for treatment and prophylaxis of hepatitis and other hepatic disorders.

22 Claims, No Drawings

DITHIOLANE DERIVATIVES

BACKGROUND OF THE INVENTION

1. Field of the Invention

The present invention relates to novel dithiolan derivatives which are effective for treatment and/or prophylaxis of liver or hepatic diseases. The present invention further relates to processes for production thereof and therapeutic compositions for hepatic diseases containing the derivatives as the effective ingredient.

2. Discussion of Related Art

It has been disclosed that compounds shown below are effective for the treatment of liver damage.

1. 1,3-dithiol-2-ylidene derivative represented by formula:

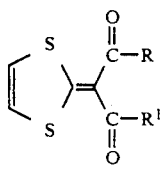

are described in U.S. Pat. No. 4,668,799 and
2dithiolane derivative represented by formula:

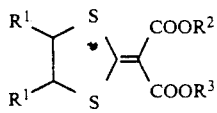

are described in Japanese Patent Application KOKAI (the term "KOKAI" is used herein to refer to an unexamined application which was laid open to public inspection) No. 63-60983; it is mentioned therein that these compounds are useful for the treatment of liver damage.

There is still a desire, however, for a compound capable of curing and/or preventing liver disorders at a considerably lower dosage which will provide a more safety margin for treating both men and animals.

SUMMARY OF THE INVENTION

An object of the present invention is to provide novel dithiolane derivatives and pharmaceutically acceptable non-toxic salts thereof, which possess liver function activating activities.

Another object of the present invention is to provide compositions for treating and/or preventing hepatic diseases which comprises as the effective ingredient the dithiolane derivatives described above.

A further object of the present invention is to provide processes for production of these dithiolane derivatives.

A dithiolane derivatives represented by the general formula (I)

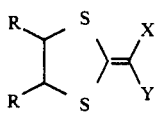

wherein X represents $C_2-C_7$ alkylcarbonyl group; benzoyl group; benzoyl group substituted with 1 to 3 groups selected from the group consisting of halogen atom, $C_1-C_4$ alkyl group and $C_1-C_4$ alkoxy group; Y represents $C_2-C_7$ alkylcarbonyl group, $C_2-C_7$ alkoxycarbonyl group or cyano group, and R represents di($C_1-C_4$ alkylamino) group, morpholino group or piperidino group.

The dithiolane derivatives represented by general formula (I) are novel compounds that are not found in publications. The dithiolane derivatives exert, for example, an activating action on liver functions and are thus effective as liver function activators or therapeutic agents for hepatic disease in human or animals.

DETAILED DESCRIPTION OF PREFERRED EMBODIMENTS

Preferred substituents for the dithiolane derivatives represented by general formula (I) in the present invention include, for X, $C_2-C_7$ alkylcarbonyl group, benzoyl group or benzoyl group substituted with halogen atom, $C_1-C_4$ alkoxy group or $C_1-C_4$ alkyl group, with particularly preferred being benzoyl group or benzoyl group substituted with chlorine atom. For Y, $C_2-C_7$ alkylcarbonyl group, $C_2-C_7$ alkoxycarbonyl group or cyano group with particularly preferred being acetyl group, ethoxycarbonyl group or isopropoxycarbonyl group. For R, di($C_1-C_4$ alkyl) amino group or morpholino group with particularly preferred being dimethylamino group or morpholino group.

The compounds represented by general formula (I) can be synthesized, for example, by the following routes, Process A and Process B.

Process A:

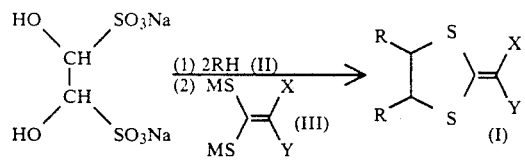

wherein R, X and Y have the same significances as described above and M represents an alkali metal atom.

That is, the compound represented by general formula (I) can be produced by reacting glyoxal sodium bisulfite adduct represented by the structural formula above with the compound represented by general formula (II) in water or in combination of water and an organic solvent, at a temperature chosen from the range between under cooling and about 80° C., and then reacting the resulting reaction mixture with the compound represented by general formula (III) at a temperature chosen from about $-20°$ C. to about 60° C.

Examples of the solvent which is used to mix with water in this process include alcohol, acetonitrile, tetrahydrofuran, dimethylformamide, dimethylsulfoxide, hexamethylphosphoramide, N,N'-dimethylethyleneurea, etc.; and a mixture of these organic solvents.

The reaction time may vary depending upon reaction temperature and reaction scale. In the reaction between glyoxal or glyoxal sodium bisulfite adduct thereof and the compound represented by general formula (II), the reaction time is appropriately chosen from the range of 10 minutes to 6 hours. Further at the step where the reaction product is reacted with the compound represented by general formula (III), the reaction time is chosen from the range of 20 minutes to 20 hours.

Each reaction proceeds stoichiometrically so that reactants may be used in equimolar amounts. However, any of the reactants may also be used in an excess amount, of course.

The compound represented by general formula (III) can be obtained in the reaction solution, as shown below, by reacting a compound represented by general formula (IV) with carbon disulfide in a polar solvent, e.g., at a temperature chosen from the range of −20° C. to 60° C., in the presence of a base. Accordingly, in many cases, the compound represented by general formula (III) is provided for the reaction in the form of a solution containing the same.

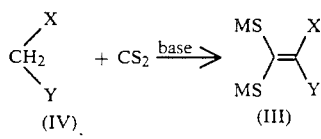

wherein X, Y and M are the same as described above.

Examples of the base which is used to synthesize the compound represented by general formula (III) include hydroxides such as sodium hydroxide, potassium hydroxide, etc. and carbonates such as sodium carbonate, potassium carbonate, etc. Examples of the solvent include dimethylformamide, dimethylsulfoxide, hexamethylphosphoramide, N,N'-dimethylethyleneurea, etc.; and a mixture of solvents selected from these organic solvents; and a mixture of water with the organic solvent described above.

As shown below, glyoxal sodium bisulfite can be obtained by adding glyoxal to sodium bisulfite in an equimolar amount or somewhat excess molar amount and reacting them in an aqueous solvent at a temperature chosen from the range between under cooling and about 80° C.

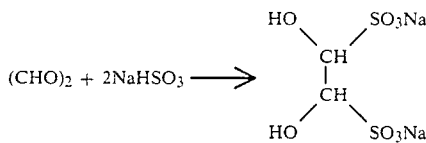

Process B

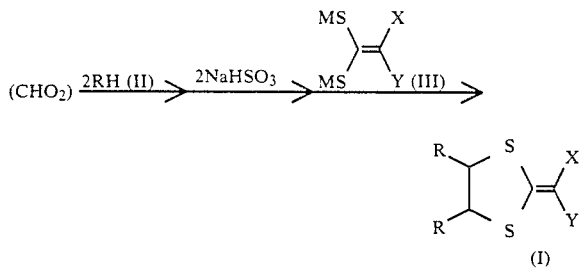

wherein R, X and Y have the same significances as described above.

That is, the compound represented by general formula (I) can be produced by reacting glyoxal with the compound represented by general formula (II) in water or a solvent mixture of water and an organic solvent, for example, at a temperature chosen from under cooling to room temperature, and then reacting the resulting mixture with sodium bisulfite, for example, at a temperature chosen from room temperature to 60° C., and further reacting with the compound represented by general formula (III), for example, at a temperature chosen from under cooling to 80° C.

Examples of the organic solvent used in this reaction include dimethylformamide, dimethylsulfoxide, hexamethylphosphoramide, N,N'-dimethylethyleneurea, etc.; and a mixture selected from these organic solvents. The reaction time may vary depending upon reaction temperature and reaction scale, but can be chosen from the range of 1 to 24 hours. Each reaction proceeds stoichiometrically so that reactants may be used in equimolar amounts. However, any of the reactants may also be used in an excess amount, of course.

By further reacting the compound represented by general formula (I) with an acid, the corresponding salts can be obtained.

The salts of the compound represented by general formula (I) may be any of pharmaceutically acceptable salts. Examples of the acid with which the compound represented by general formula (I) is reacted in order to form the salts include inorganic acids such as hydrochloric acid, sulfuric acid, phosphoric acid, etc.; organic carboxylic acids such as acetic acid, succinic acid, fumaric acid, tartaric acid, etc.; alkanesulfonic acids such as methanesulfonic acid, heptanesulfonic acid, etc. and arylsulfonic acids such as benzenesulfonic acid, toluenesulfonic acid, etc.

As the solvent used for forming the salts of the compound represented by general formula (I), mention may be made of, for example, water, alcohol, tetrahydrofuran, acetone, ether, ethyl acetate, methylene dichloride, chloroform, etc.

After completion of the reaction, the reaction mixture is treated in a conventional manner to give the compound represented by general formula (I) and salts thereof.

Representative examples of the compound represented by general formula (I) or salts thereof are shown in Table 1 below.

TABLE 1

| Compound No. | X | Y | R | Physical Property [melting point or refractive index] |
| --- | --- | --- | --- | --- |
| 1 | −C(=O)−CH₃ | −COOCH₃ | −N(CH₃)₂ | m.p. 111–114° C. |
| 2 | −C(=O)−CH₃ | −COOC₂H₅ | −N(CH₃)₂ | m.p. 87–88° C. |

TABLE 1-continued

| Compound No. | X | Y | R | Physical Property [melting point or refractive index] |
|---|---|---|---|---|
| 3 | −C(=O)−CH₃ | −COOC₃H₇-n | −N(CH₃)₂ | m.p. 74–75° C. |
| 4 | −C(=O)−CH₃ | −COOC₃H₇-i | −N(CH₃)₂ | m.p. 63–65° C. |
| 5 | −C(=O)−CH₃ | −COOC₄H₉-n | −N(CH₃)₂ | $n_D^{29}$: 1.5721 |
| 6 | −C(=O)−CH₃ | −COOC₂H₅ | −N(morpholino) | m.p. 116–119° C. |
| 7 | −C(=O)−CH₃ | −COOC₃H₇-n | −N(morpholino) | m.p. 100–105° C. |
| 8 | −C(=O)−CH₃ | −COOC₃H₇-i | −N(morpholino) | m.p. 134–137° C. |
| 9 | −C(=O)−CH₃ | −C(=O)−CH₃ | −N(morpholino) | m.p. 150–153° C. |
| 10 | −C(=O)−C₆H₅ | −C(=O)−CH₃ | −N(CH₃)₂ | m.p. 123–125° C. |
| 11 | −C(=O)−C₆H₄−Cl (4-) | −C(=O)−CH₃ | −N(CH₃)₂ | m.p. 130–132.5° C. |
| 12 | −C(=O)−C₆H₄−Cl (2-) | −C(=O)−CH₃ | −N(CH₃)₂ | m.p. 108–110° C. |
| 13 | −C(=O)−C₆H₄−CH₃ (4-) | −C(=O)−CH₃ | −N(CH₃)₂ | m.p. 140–143° C. |
| 14 | −C(=O)−C₆H₄−OCH₃ (4-) | −C(=O)−CH₃ | −N(CH₃)₂ | m.p. 148–149° C. |
| 15 | −C(=O)−C₆H₅ | −C(=O)−CH₃ | −N(4-methylpiperazino) (−N−NCH₃) | m.p. 181–183° C. |
| 16 | −C(=O)−C₆H₄−Cl (4-) | −C(=O)−CH₃ | −N(morpholino) | m.p. 131–132° C. |

TABLE 1-continued

| Compound No. | X | Y | R | Physical Property [melting point or refractive index] |
|---|---|---|---|---|
| 17 | 3,4-dimethoxybenzoyl (−C(=O)−C₆H₃(OCH₃)₂) | −C(=O)−CH₃ | −N(morpholine) | m.p. 87.5–92° C. |
| 18 | −C(=O)−CH₃ | −COOC₃H₇-i | −N(CH₃)₂ | m.p. 152–154.5° C. 2HCl salt |
| 19 | 2-chlorobenzoyl (−C(=O)−C₆H₄Cl) | −C(=O)−CH₃ | −N(CH₃)₂ | m.p. 139–143° C. 2HCl salt |
| 20 | −C(=O)−CH₃ | −COOC₃H₇-i | −N(morpholine) | m.p. 166–170° C. 2HCl salt |
| 21 | benzoyl (−C(=O)−C₆H₅) | −COOC₂H₅ | −N(CH₃)₂ | m.p. 148–150° C. |
| 22 | benzoyl (−C(=O)−C₆H₅) | −C(=O)−CH₃ | −N(piperidine) | m.p. 146.3° C. |
| 23 | 2-chlorobenzoyl (−C(=O)−C₆H₄Cl) | −C(=O)−CH₃ | −N(morpholine) | m.p. 129–131° C. |
| 24 | 4-methylbenzoyl (−C(=O)−C₆H₄CH₃) | CN | −N(CH₃)₂ | m.p. 164–166° C. |
| 25 | 4-methoxybenzoyl (−C(=O)−C₆H₄OCH₃) | CN | −N(CH₃)₂ | m.p. 151–152° C. |
| 26 | 3-chlorobenzoyl (−C(=O)−C₆H₄Cl) | CN | −N(CH₃)₂ | m.p. 128–129° C. |
| 27 | 4-methoxybenzoyl (−C(=O)−C₆H₄OCH₃) | CN | −N(morpholine) | m.p. 170–174° C. |
| 28 | 4-tert-butylbenzoyl (−C(=O)−C₆H₄C₄H₉-t) | CN | −N(morpholine) | m.p. 140–147° C. |

TABLE 1-continued

| Compound No. | X | Y | R | Physical Property [melting point or refractive index] |
|---|---|---|---|---|
| 29 | -C(=O)-C6H2(OCH3)3 (3,4,5-trimethoxybenzoyl) | CN | -N(morpholino) | m.p. 95–99° C. |
| 30 | -C(=O)-C4H9-t | CN | -N(morpholino) | m.p. 84–87° C. |
| 31 | -C(=O)-CH3 | -COOC3H7-i | -N(piperidino) | m.p. 101.5° C. |

The melting point of the compound numbers 18–20 in the Table 1 shows the value of hydrochloric acid salt of said compounds.

Next, the present invention is described with reference to examples below but is not deemed to be limited thereto

EXAMPLE 1 n-Propyl 2-((4,5-bis(dimethylamino)-1,3-dithiolan)-2-ylidene)acetoacetate (Compound No. 3)

n-Propyl acetoacetate, 2.88 g (0.020 mol), was dissolved in 20 ml of dimethylformamide and, 1.82 g (0.024 mol) of carbon disulfide and 3.60 g (0.026 mol) of anhydrous potassium carbonate powders were added to the solution. The mixture was stirred at room temperature for an hour to prepare a dithiolate solution. On the other hand, 6.84 g (0.024 mol) of glyoxal sodium bisulfite adduct was suspended in 30 ml of water in a separate flask and 5.4 g (0.060 mol) of dimethylamine (50% aqueous solution) was dropwise added to the suspension, while cooling below 0° C. The mixture was stirred until the mixture became a homogeneous solution. The dithiolate solution previously prepared was dropwise added to the resulting solution. The mixture was then stirred for 30 minutes below 0° C. Thereafter, the reaction liquid was poured onto ice water and the precipitated crystals were collected by filtration and air dried. Crude crystals were purified by silica gel chromatography and then recrystallized from ether-n-hexane to give 0.84 g of the objective product.

m.p. 74.5° C.; yield, 12.6%.

EXAMPLE 2

Isopropyl 2-((4,5-dimorpholino-1,3-dithiolan)-2-ylidene)acetoacetate (Compound No. 8)

Isopropyl acetoacetate, 2.88 g (0.020 mol), was dissolved in 20 ml of dimethylsulfoxide and, 2.0 g (0.026 mol) of carbon disulfide and 3.60 g (0.026 mol) of anhydrous potassium carbonate powders were added to the solution. The mixture was stirred at room temperature for an hour to prepare a dithiolate solution. On the other hand, 6.84 g (0.024 mol) of glyoxal sodium bisulfite adduct was taken in a separate flask and suspended in 30 ml of water. Then, 6.26 g (0.072 mol) of morpholine was dropwise added to the suspension. The mixture was stirred at room temperature until the mixture became a homogeneous solution Next, the dithiolate solution previously prepared was dropwise added to the resulting solution, while cooling the solution with a coolant. The mixture was stirred for 30 minutes. The reaction liquid was poured onto ice water and the precipitated crystals were collected by filtration and air dried. Crude crystals were dissolved in ethyl acetate After insoluble matters were removed, recrystallization was performed from ethyl acetate-n-hexane to give 1.90 g of the objective product.

m.p. 134°–137° C.; yield, 23.0%.

EXAMPLE 3

2-((4,5-Bis(dimethylamino)-1,3-dithiolan)-2-ylidene)-1-phenylbutan-1,3-dione (Compound No. 10)

Benzoylacetone, 1.65 g (0.10 mol), was dissolved in 50 ml of dimethylsulfoxide. Under ice cooling, 14.5 g (0.11 mol) of anhydrous potassium carbonate powders were added to the solution An ice bath was withdrawn and 7.6 g (0.10 mol) of carbon disulfide was dropwise added to the mixture at 20° to 25° C. The mixture was stirred for an hour to prepare a dithiolate solution On the other hand, 34 g (0.12 mol) of glyoxal sodium bisulfite adduct was taken in a separate flask and suspended in 125 ml of water. The suspension was cooled to below 0° C. and 33 g (0.36 mol) of 40% dimethylamine aqueous solution was dropwise added to the suspension followed by stirring for 15 minutes. The dithiolate solution previously prepared was dropwise added to the resulting solution The mixture was stirred for 30 minutes After 100 ml of water was added thereto, the reaction mixture was extracted with ethyl acetate. After the extract was dried over anhydrous sodium sulfate, the solvent was distilled off to give a brown viscous material The viscous material was purified by silica gel chromatography and then recrystallized from ethyl acetate-n-hexane to give 7.8 g of the objective product m.p. 123°–125° C.; yield, 22%.

EXAMPLE 4

2-((4,5-Dimorpholino-1,3-dithiolan)-2-ylidene)-1-(4-chlorophenyl)butan-1,3-dione (Compound No. 16)

4-Chlorobenzoylacetone, 4.42 g (0.020 mol) and 1.60 g (0.021 mol) of carbon disulfide were dissolved in 15 ml of dimethylsulfoxide. Under ice cooling, 3.0 g of anhydrous potassium hydroxide powders were added to the solution An ice bath was withdrawn and the mixture was stirred for an hour at room temperature. The resulting solution was dropwise added at 0° C. to a homogeneous solution prepared from 5.72 g (0.014 mol) of glyoxal sodium bisulfite adduct, 3.90 g (0.044 mol) of morpholine and 20 ml of water. After stirring for an hour, the reaction mixture was extracted with ethyl acetate. After the extract was dried over anhydrous sodium sulfate and concentrated to give a brown viscous material. The viscous material was recrystallized from ether to give 2.7 g of the objective product.

m.p. 131°–132° C.; yield, 31%

2-((4,5-dimorpholino-1,3-dithiolan)-2-ylidene)-1-(2-chlorophenyl)butan-1,3-dione was also synthesized in the same manner as described above except that 2-chlorobenzolyacetone was used instead of 4-chlorobenzolyacetone.

EXAMPLE 5

1-((4,5-Dimorpholino-1,3-dithiolan)-2-ylidene)-1-(4-methoxybenzoyl)-acetonitrile (Compound No. 27)

A solution prepared from 1.75 g (0.010 mol) of 4-methoxybenzoylacetonitrile, 0.90 g (0.012 mol) of carbon disulfide, 4.85 g of 30% potassium hydroxide aqueous solution and 10 ml of acetone was dropwise added to a solution prepared from 2.84 g (0.010 mol) of glyoxal sodium bisulfite adduct, 1.91 g (0.022 mol) of morpholine and 10 ml of water, under ice cooling. The mixture was stirred for 20 minutes. The reaction mixture was then post-treated in a conventional manner to give 1.70 g of the objective product.

m.p. 170°–174° C. (chloroform-ether); yield, 38%.

EXAMPLE 6

Isopropyl 2-((4,5-bisdimethylamino-1,3-dithiolan)-2-ylidene)acetoacetate dihydrochloride (Compound No. 18)

Isopropyl 2-(4,5-bisdimethylamino-1,3-dithiolan-2-ylidene)acetoacetate, 3.0 g (0.008 mol) was dissolved in 20 ml of acetic acid. Dry hydrogen chloride gas was gently blown into the solution at room temperature to saturation. The reaction mixture was ice cooled and precipitated crystals were taken by filtration. The crystals were thoroughly washed with ethyl acetate and ether to give 2.8 g of the objective product.

m.p. 152-154.5° C; yield, 78%.

The compounds represented by general formula (I) and pharmaceutically acceptable salts thereof have such a low toxicity that even when these compounds are administered to mice in a dose of 300 mg/kg/day for consecutive several days, the mice neither show toxic symptoms nor die.

The compounds represented by general formula (I) and salts thereof are useful as drugs for curing hepatic diseases. For example, it is known that hepatic disorders can be caused in an experimental animal by giving various chemicals such as carbon tetrachloride, etc. (for example, Japanese Published Patent Application KOKOKU No. 18579/1981). It has been found that the compounds represented by general formula (I) and salts thereof show marked inhibitory or improving effects against reduced liver functions in the animal suffering from experimental hepatic disturbances of various morbid models, when administered orally or parenterely (e.g., injection). Therefore, the compounds represented by general formula (I) and salts thereof are useful as drugs applied to human and animals for treatment or prophylaxis of hepatic diseases. That is, the compounds can be used as agents for treating acute or chronic liver diseases which occur on human or animal due to various causes, for example, fatty liver, alcohol-induced hepatitis, hepatitis, intoxicative liver diseases, congestion of liver, bile congestive hepatic disturbance or, liver cirrhosis which is the terminal pattern of these diseases.

Accordingly, the term "drug for treatment of hepatic diseases" as used in the present specification refers to a drug for treatment or/and prophylaxis of hepatic diseases utilizing pharmacological activities such as the aforesaid liver function activating activity exerted on liver and prophylactic and therapeutic activities of hepatic diseases, etc.

The compounds represented by general formula (I) and salts thereof can be used as they are, as drugs for curing hepatic diseases. It is also possible to formulate them into mixtures with pharmaceutically acceptable diluents and/or other pharmacologically active ingredients according to pharmaceutical custom. Furthermore, they can also be formulated into dosage unit forms. Forms which they can have as drugs include powders, granules, tablets, dragees, capsules, pills, suspensions, solutions, emulsions, ampoules, injections, isotonic solutions, etc.

Formulation of the compound of this invention into a medicinal composition includes an embodiment in which the compound represented by general formula (I) or salts thereof is incorporated into the composition in the form of a mixture with pharmaceutically acceptable diluents. The term "diluents" used herein means materials other than the compound represented by general formula (I) and salts thereof. The diluents may be any of solids, semisolids, liquids and ingestible capsules and include various materials, for example, excipients, extenders, binders, wetting agents, disintegrators, surfactants, lubricants, dispersants, buffers, taste-improver, odor-reducing agents, coloring matters, flavors, preservatives, dissolution assistance, solvents, coatings, frostings, etc. But the diluents are not limited thereto. These materials are used alone or as a mixture thereof. Such pharmaceutically acceptable diluents are used as a mixture with other pharmacologically active ingredients in some cases.

A medicinal composition using the compound of this invention may be produced by any known method. For example, the active ingredient is mixed with diluents to yield, for instance, granules, and then the composition thus obtained is formed, for example, into tablets. When the medicinal composition is used as a parenteral drug, it should be sterilized. If necessary, it should be made isotonic with regard to blood.

In this invention, since the compounds represented by above general formula (I) and salts thereof are per se applicable as drugs for curing hepatic diseases, the active ingredient is contained in the composition usually in an amount of 0.01 to 100% (by weight).

When the compound or salts thereof of this invention is formulated into a preparation of dosage unit, individual pharmaceutical portions constituting said preparation may be either in different forms or in the same forms, and there are often employed, for example, forms such as tablets, granules, pills, powders, dragees, capsules, and ampoules.

The drugs for curing hepatic diseases according to this invention can be applied to human beings and animals in order to prevent and cure hepatic disorders, by a method which is conventional in the fields of such prevention and therapy. They are administered orally or parenterally. The oral administration includes sublingual administration. The parenteral administration includes administration by injection (including, for example, subcutaneous injection, intramuscular injection, intravenous injection, and drip).

The dose of the drugs of this invention is varied depending various factors such as animals or human beings of subject, sensitivity difference, age, sex and body weight, the administration route, time and interval of administration, condition of a disease, physical condition of the subject, properties of pharmaceutical preparation, kind of preparation, kind of active ingredient, etc.

Therefore, in some cases, a dose smaller than the minimum dose described below is sufficient, and in other cases, a dose larger than the maximum dose described below is required.

In the case of a high dose, administration in several times a day is preferred.

In order to obtain effective results for animals, the dose in terms of the active ingredient is advantageously 0.1 to 300 mg, preferably 0.1 to 30 mg per kg of body weight per day in the case of oral administration, while in the case of parenteral administration, it is advantageously 0.01 to 250 mg, preferably 0.1 to 25 mg per kg of body weight per day.

In order to obtain effective results for human beings, in consideration of sensitivity difference, safety, etc. on the basis of the effective dose for animals, the dose for human beings seems to be advantageously, for example, in the following ranges: in the case of oral administration, 0.1 to 200 mg, preferably 0.5 to 50 mg per kg of body weight per day, and in the case of parenteral administration, 0.01 to 100 mg, preferably 0.1 to 25 mg per kg of body weight per day.

Hereafter, several examples of medical formulations are shown below but the present invention is not deemed to be limited thereto.

In the following formulation examples, all parts are by weight.

| Formulation Example 1 | |
|---|---|
| Compound 2 | 10 parts |
| Heavy magnesium oxide | 10 parts |
| Lactose | 80 parts |

A powder or fine granular preparation was prepared by mixing uniformly and pulverizing or granulating finely the above ingredients.

| Formulation Example 2 | |
|---|---|
| Compound 10 | 10 parts |
| Synthetic aluminum silicate | 10 parts |
| Calcium hydrogenphosphate | 5 parts |
| Lactose | 75 parts |

A powder was prepared according to Formulation Example 1 by using the above ingredient.

| Formulation Example 3 | |
|---|---|
| Compound 12 | 50 parts |
| Starch | 10 parts |
| Lactose | 15 parts |
| Crystalline cellulose | 20 parts |
| Polyvinyl alcohol | 5 parts |
| Water | 30 parts |

Granules were prepared by kneading together uniformly, grinding, granulating the above ingredients, drying the resultant, and then sieving.

Formulation Example 4

Tablets having a diameter of 10 mm were prepared by mixing 99 parts of the granules obtained in Formulation Example 3 with 1 part of calcium stearate, and compression-molding the resulting mixture.

| Formulation Example 5 | |
|---|---|
| Compound 19 | .78 parts |
| Polyvinyl alcohol | 2 parts |
| Lactose | 20 parts |
| Water | 30 parts |

Granules were prepared in the same manner as in Formulation Example 3 except for using the above ingredients. To 90 parts of the granules obtained was added 10 parts of crystalline cellulose, and the resulting mixture was compression-molded into tablets having a diameter of 8 mm. Then, the tablets were made into dragees by use of suitable amounts of a mixed suspension of syrup, gelatin and precipitated calcium carbonate and coloring matter.

| Formulation Example 6 | |
|---|---|
| Compound 27 | 0.5 parts |
| Nonionic surface active agent | 2.5 parts |
| Physiological saline | 97 parts |

An injection was prepared by mixing by heating, and then sterilizing the above ingredients.

Formulation Example 7

Capsules were prepared by packing the powder obtained in Formulation Example 1 into commercially available capsular containers.

Next, in order to prove the effectiveness of the compounds of this invention, test example is shown below.

Test Example 1

Effect of inhibiting carbon tetrachloride-induced hepatic disorders

Method

A test compound was dissolved or suspended in olive oil and the resulting solution or suspension was orally administered to male mice (6 week age) of dd strain in a dose of 30 mg/kg. Six hours after the administration, carbon tetrachloride was orally administered to the mice in a dose of 0.05 ml/kg. The mice were sacrificed 24 hours after the administration of carbon tetrachloride. Degree of hepatic disorders was visually examined.

On the other hand, blood was collected when they were sacrificed and plasma was obtained by centrifugation. Plasma glutamic-pyruvic transaminase (GPT) activity was determined according to the Reitman-Frankel method and the activity was expressed by Karmen Unit (K.U.). The hepatic disorder index is evaluated as below.

| Hepatic Disorder Index | Condition of Liver |
|---|---|
| 0 | Healthy liver |
| 2 | Slightly influenced |
| 4 | Disorder was obviously noted. |
| 6 | Heavy disorder |

Five (5) mice were used in each group and the results are shown by a mean value. Further with respect to GPT activity, no further measurement was conducted with the case showing more than 2,100 units but for brevity, it was calculated as 2,100 units. The results are shown in Table 2.

TABLE 2

| Activity on Carbon Tetrachloride-Induced Hepatic Disorder | | |
|---|---|---|
| Compound No. of This invention | Hepatic Disorder Index | p-GPT (K.U.) |
| Single Administration of Carbon Tetrachloride | 5.4 | >2,100 |
| Intact | 0 | |
| Compound No. 2 | 0.8 | 16 |
| Compound No. 4 | 0.6 | 18 |
| Compound No. 8 | 0.8 | 13 |
| Compound No. 9 | 1.0 | 90 |
| Compound No. 10 | 0.7 | 18 |
| Compound No. 11 | 0 | 17 |
| Compound No. 14 | 1.5 | 96 |
| Compound No. 19 | 2.8 | 218 |
| Compound No. 23 | 1.0 | 93 |
| Compound No. 27 | 0.2 | 41 |
| reference compound A | 1.6 | 861 | reference compound A:

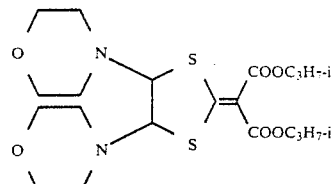

compound disclosed in Japanese Patent Application KOKAI 63-60983

As is noted from the results above, the compounds of this invention show activating action on liver functions and are thus effective as liver function activaters or therapeutic agents for hepatic disease in human or animal.

While the invention has been described in detail and with reference to specific embodiments thereof, it will be apparent to one skilled in the art that various changes and modifications can be made therein without departing from the spirit and scope thereof.

What is claimed is:

1. A dithiolane derivative represented by the general formula (I)

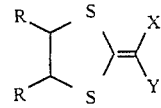

wherein X represents $C_2$-$C_7$ alkylcarbonyl group; benzoyl group or benzoyl group substituted with 1 to 3 groups selected from the group consisting of halogen atom, $C_1$-$C_4$ alkyl group and $C_1$-$C_4$ alkoxy group; Y represents $C_2$-$C_7$ alkylcarbonyl group, $C_2$-$C_7$ alkoxycarbonyl group or cyano group and R represents di($C_1$-$C_4$ alkyl)amino group or morpholino group.

2. A dithiolane derivative or pharmaceutically acceptable salt thereof according to claim 1, wherein X represents $C_2$-$C_5$ alkylcarbonyl group, Y represents $C_2$-$C_5$ alkylcarbonyl group, $C_2$-$C_5$ alkoxycarbonyl group or cyano group, and R represents di($C_1$-$C_4$ alkyl)amino group or morpholino group.

3. A dithiolane derivative or pharmaceutically acceptable salt thereof according to claim 1, wherein X represents benzoyl group or benzoyl group substituted with halogen atom, $C_1$-$C_4$ alkyl group or $C_1$-$C_4$ alkoxy group; Y represents $C_2$-$C_5$ alkylcarbonyl group or cyano group, and R represents di($C_1$-$C_4$ alkyl)amino group or morpholino group.

4. A dithiolane derivative or pharmaceutically acceptable salt thereof according to claim 1 or 2, wherein X represents, acetyl group, Y represents ethoxycarbonyl group or isopropoxycarbonyl group, and R represents dimethylamino group or morpholino group.

5. A dithiolane derivative or pharmaceutically acceptable salt thereof according to claim 1 or 3, wherein X represents benzoyl group or benzoyl group substituted with chlorine atom; Y represents acetyl group or cyano group, and R represents dimethylamino group or morpholino group.

6. A dithiolane derivative as in any one of claim 1, 2 or 4 which is isopropyl 2-((4,5-bis(dimethylamino)-1,3-dithiolan)-2-ylidene)acetoacetate.

7. A dithiolane derivative as in any one of claim 2 or 4 which is isopropyl 2-((4,5-dimorpholino-1,3-dithiolan)-2-ylidene)acetoacetate.

8. A dithiolane derivative as in any one of claim 1, 3 or 5 which is 2-((4,5-dimorpholino-1,3-dithiolan)-2-ylidene)-1-(4-chlorophenyl)butan-1,3dione.

9. A dithiolane derivative as in any one of claim 1, 3 or 5 which is 2-((4,5-dimorpholino-1,3-dithiolan)-2-ylidene)-1-(2-chlorophenyl)butan-1,3-dione.

10. A dithiolane derivative as in any one of claim 1, 3 or 5 which is 2-((4,5-bis(dimethylamino)-1,3-dithiolan)-2-ylidene)-1-phenylbutan-1,3-dione.

11. A dithiolane derivative as in any one of claim 1, 3 or 5 which is 2-((4,5-dimorpholino-1,3-dithiolan)-2-ylidene)-1-(4-methoxybenzoyl)-acetonitrile 12. A composition for treating hepatic disease comprising as an effective ingredient a dithiolane derivative represented by the general formula (I):

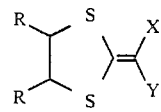

wherein X represents $C_2$-$C_7$ alkylcarbonyl group, benzoyl group or benzoyl group substituted with 1 to 3 groups selected from the group consisting of halogen atom, $C_1$-$C_4$ alkyl group and $C_1$-$C_4$ alkoxy group; Y represents $C_2$-$C_7$ alkylcarbonyl group, $C_2$-$C_7$ alkoxycarbonyl group or cyano group, and R represents di($C_1$-$C_4$ alkyl)amino group or morpholino group.

13. A composition for treating hepatic disease according to claim 12, wherein X represents $C_2$-$C_5$ alkylcarbonyl group Y represents $C_2$-$C_5$ alkylcarbonyl group, $C_2$-$C_5$ alkoxycarbonyl group or cyano group, and R represents di(Cl-C4 alkyl)amino group or morpholino group.

14. A composition for treating hepatic disease according to claim 12, wherein X represents benzoyl group or benzoyl group substituted with halogen atom, $C_1$-$C_4$ alkyl group or $C_1$-$C_4$ alkoxy group; Y represents $C_2$-$C_5$ alkylcarbonyl group or cyano group, and R represents di($C_1$-C4 alkyl)amino group or morpholino group.

15. A composition for treating hepatic disease according to claim 12 or 13, wherein X represents acetyl group, Y represents ethoxycarbonyl group or isopropoxycarbonyl group, and R represents dimethylamino group or morpholino group.

16. A composition for treating hepatic disease according to claim 12 or 14 wherein X represents benzoyl group or benzoyl group substituted with chlorine atom; Y represents acetyl group or cyano group, and R represents dimethylamino group or morpholino group.

17. A pharmaceutical composition in any one of claim 12, 13 or 15 which is isopropyl 2-((4,5-bis(dimethylamino)-1,3-dithiolan)-2-ylidene)acetoacetate.

18. A pharmaceutical composition as in any one of claims 12, 13 or 15 which is isopropyl 2-(4,5-dimorpholino-1,3-dithiolan-2-ylidene)acetoacetate.

19. A pharmaceutical composition as in any one of claims 12, 14 or 16 which is 2-((4,5-dimorpholino-1,3-dithiolan)-2-ylidene)-1-(4-chlorophenyl)butan-1,3-dione.

20. A pharmaceutical composition as in any one of claim 12, 14 or 16 which is 2-((4,5-dimorpholino-1,3-dithiolan)-2-ylidene)-1-(2-chlorophenyl)butan-1,3-dione.

21. A pharmaceutical composition as in any claim 12, 14 or 16 which is 2-((4,5-bis(dimethylamino)-1,3-dithiolan)-2-ylidene)-1-phenylbutan-1,3-dione.

22. A pharmaceutical composition as in any one of claims 12, 14 or 16 which is 2-((4,5-dimorpholino-1,3-dithiolan)-2-ylidene)-1-(4-methoxybenzoyl)acetonitrile.

* * * * *